United States Patent [19]

Palacios

[11] Patent Number: 5,256,406
[45] Date of Patent: Oct. 26, 1993

[54] TREATMENT OF HAIR LOSS AND DERMATOLOGICAL PROBLEMS

[76] Inventor: Henry J. Palacios, 8005 Algarve St., McLean, Va. 22102

[21] Appl. No.: 810,863

[22] Filed: Dec. 20, 1991

Related U.S. Application Data

[63] Continuation-in-part of Ser. No. 727,861, Jul. 10, 1991, abandoned.

[51] Int. Cl.$^5$ ............................................... A61K 7/06
[52] U.S. Cl. ........................................ 424/70; 424/91; 424/400; 424/434; 424/435
[58] Field of Search ............... 424/70, 91, 434, 435, 424/400; 514/230.2; 436/506, 534, 817; 552/638

[56] References Cited

U.S. PATENT DOCUMENTS 4,980,358 12/1990 Smith ............................... 514/230.2

OTHER PUBLICATIONS

Martindale The Extra Pharmacopoeia; 26th Edition, 1972; The Pharmaceutical Press, pp. 1691–1692.
The United States Pharmacopeia; 21st Edition, 1985 p. 1027.
Allergy Management in Clinical Practice, Louis Tuft, 1973; Mosby Company, pp. 73–77.

Primary Examiner—Thurman K. Page
Assistant Examiner—William E. Benston
Attorney, Agent, or Firm—Glenna Hendricks

[57] ABSTRACT

It has been found that loss of hair and malfunction of the lubricating function of the skin can be treated with small mounts of testosterone or house dust antigen given in desensitizing doses. Treatment with minidoses of testosterone or house dust suspensions is relatively inexpensive.

19 Claims, No Drawings

TREATMENT OF HAIR LOSS AND DERMATOLOGICAL PROBLEMS

This is a continuation-in-part of patent application Ser. No. 07/727,861 filed Jul. 10, 1991, now pending.

This invention provides a means of treating hair loss and other dermatological problems of allergenic origin using desensitizing doses of allergens.

BACKGROUND OF THE INVENTION

The treatment of dermatological problems related to hair loss has been a topic of considerable study. The most widely used treatment at the present time is topical application of minoxidil (Rograine TM) for restoration of hair loss on the crown of the head of individuals with male pattern androgenic baldness of hereditary origin. The method has several disadvantages. The hair produced is usually short, thin, and often discolored. The hair loss resumes as soon as the treatment is discontinued. The treatment does not alleviate unattractive appearance of hair that arises from abnormally dry or oily scalp. Moreover, the use of minoxidil is effective in only 10% to 20% of the patients suffering from hair loss.

There have been reports of treatment of premenstrual syndrome using minidoses of progesterone as desensitizing allergens. No previous disclosure of use of minidoses of androgens to relieve dermatological problems of dryness, abnormal oil production and distribution, or hair loss has been reported.

DESCRIPTION OF THE INVENTION

This inventor had noted that allergy treatment for sinus and nasal conditions frequently resulted in improved moisture of the skin and improved hair production and retention. However, when specific allergic response to specific antigens more commonly used for treatment of allergies was not indicated, or when such treatment did not result in effective treatment of hair loss and other dermatological problems of dryness or inappropriate oil production and distribution in the skin, treatment with testosterone or house dust suspensions often proved to be highly beneficial. The dosage is individualized in accord with the teachings disclosed herein.

It is the purpose of this invention to provide means of treating hair loss and skin problems by administration of very small doses of testosterone or house dust allergens. While it has been common to treat specific food and inhalant allergies with desensitizing doses of specific food, pollen, and other antigenic materials, the use of house dust suspensions is little used today to treat allergic symptoms. It has now been found that many patients suffering from hair loss and other dermatologic malfunction, in particular from dry scalp and abnormal distribution of oil, suffer from either allergy to house dust or allergic response to testosterone.

It has also been found that when there is a familial history of hair loss and abnormal lubricating function of the skin, treatment using minidoses of testosterone to treat the chronic allergic conditions can be of great value in restoring hair production and retention and in improving skin condition. The hair distribution resulting from the treatment disclosed herein is normal. Furthermore, the hair produced in response to this treatment was attractive and normal in appearance and was retained for a considerable period of time after the treatment is discontinued. The skin of the patient treated by the methods of the invention is usually soft and well lubricated.

Treatment with minidoses of testosterone or house dust suspensions is relatively inexpensive. The testosterone therapy is easily administered by the patient without use of equipment required for injection.

EXAMPLE

Testosterone Therapy

When the patient is believed to suffer from testosterone allergy, the method of determining the appropriate dosage is essentially the same as that used in determining appropriate dosage for use in any regimen involving desensitization therapy by administration of neutralizing doses of allergens. The optimal dosage is usually in the range of 0.0006 to 2 mg. per day administered once daily sublingually. When administered by this route, the medication is usually absorbed in about 30 seconds. The patient who is allergic to testosterone will usually show symptoms of hypersensitivity to the highest dosage. Any ester of testosterone or testosterone itself may be used in the manner exemplified so along as an aqueous suspension can be prepared that will be readily absorbed through the mucosa. Examples of such esters are the alkyl and cycloalkyl esters of 1-6 carbons, which may be branched or substituted with a phenyl substituent.

During testing, the patient should be placed in a quiet environment where he is made as comfortable and relaxed as possible. A dose of testosterone is then administered sublingually, and the patient is asked to indicate any symptoms that appear after administration of the testosterone. Symptoms most frequently reported are headache, drowsiness, inability to concentrate, tiredness, sudden lack of energy, sweating of the palm of the hands, visual disturbances of any kind (including blurring) or a light headed feeling. Any dosage that causes such a symptom is considered a provoking dose and is deemed excessive. It should be noted that all of the mentioned symptoms are common to persons suffering acute allergic reactions. An appropriate dose is that at which symptoms of allergy are no longer experienced after administration.

If the patient is currently suffering from symptoms of allergy such as sinus problems, migraine headaches, nasal stuffiness, hot flashes, joint stiffness, inability to concentrate, anxiety, or visual disturbances before administration of the testosterone, he may actually note a relief of symptoms within up to 30 minutes after administration. Such relief would indicate that the dose administered is a desensitizing dose. Any change is condition should be taken into consideration. The appropriate dose is that at which pre-existing allergic symptoms disappear.

The process of determination of appropriate dosage usually is inaugurated using a dose of 0.05 ml of an aqueous composition containing 20 mg per ml. of testosterone to deliver a dose of 1 mg. The testosterone is then administered daily in successive 1:4 dilutions using 1 ml of the last concentration to 4 ml of distilled water to be continued until the appropriate dosage is reached. The smallest dosage used is 0.0006 mg. For purposes of this application, the dosage will be delineated #1 to #7, with #1 being a dose of 1 mg. and #7 being 0.0006 mg. It may, thereafter, be wise to further optimize the dosage by administration of 0.1 ml, 0.15 ml or 0.2 ml of a dose near the end point at which adverse allergic symptoms are relieved or at which symptoms of acute allergic response no longer occur.

The response of individuals to antigens varies greatly. The most commonly used dosage is taught herein merely as a guide to most common usage. In fact, the treatment described herein will be found, in some individuals, to require much lower dosages than provided with dilution #7. It must be stressed that in each and every case the individual dosage should be individually determined using the methods taught herein with continuing serial dilutions until appropriate dosage is determined.

It is also possible to determine appropriate dosage using an electronic medical device for determining appropriate dosage of homeopatic medication and antigens. An example of such a device is the Vega machine made in German. That device is designed particularly to determine optimum dosage of homeopatic medications and of foods and inhalant antigens used in the treatment of food and respiratory allergies. The device uses electric currents in the body to establish the amount of the allergens compatible with the needs and tolerance levels of each patient.

It is important, in determining correct dosage, that the practitioner avoid all suggestion of symptoms that are expected in the evaluation. The most common dosage dilutions found to be useful for treatment are #2 (4 mg/ml) for a dose of 0.2 mg in 0.05 ml or #3 (0.8 mg/ml) for a dose of 0.04 mg in 0.05 ml. for men and #3 or #4 (0.16 mg/ml) for a dose of 0.008 mg. in 0.05 ml. for women. During testing, one in 10 subjects did not react at all to the testosterone testing the first time. However, on repetition, 50% of these subjects did respond. At #7 the concentration of testosterone is 0.0012 mg/ml.

Once the appropriate treatment dosage is determined, the subject is advised to administer that dosage once a day and to report any change in hair loss and/or skin condition. When noticeable improvement occurs, the dosage is continued for two months after which the frequency of administration may be decreased to every other day (q.o.d.). If no advantage is lost at the q.o.d. frequency of administration, that regimen is continued indefinitely. If there is increase in hair loss or malfunction of skin lubrication, the daily administration is resumed. After a period of sustained improvement, even lower dosages may be tried.

When improvement is lacking or insufficient, the dosage may be increased every four or five days by 0.05 ml of the dilution prescribed up to a maximum of 0.25 ml. If that dosage is insufficient, the dosage will be increased by moving to the next stronger dilution of the testosterone. The same method of increasing dosage is used if the hair growth and retention is not sustained.

If the dosage given provokes an untoward symptom, it is an indication that a provoking dose has been administered. At that time, administration of the next weaker dosage should be instituted.

The method of treatment described herein has also been used successfully for men suffering from hormonally caused sexual disfunction. For best results, the appropriate dosage should be taken between 10 and 60 minutes prior to intercourse. When used in accord with the teachings herein improvement of varying degree has been noted in 40% of males.

EXAMPLE

House Dust Antigen

Many dermatologic problems that cause hair loss and scalp problems result from allergies. Allergy to house dust appears to be a very common cause of such dermatologic problems. The use of house dust antigen in desensitizing doses in accord with the teachings herein often offers relief from symptoms of hair loss and dry scalp.

The patients were first tested for hypersensitive response to house dust in the usual manner by intradermal administration. If hypersensitivity was evidenced, the treatment protocol is initiated.

House dust antigen in suspension has been used for many years. The product of two manufacturers, Alpyral (brand name), made by Hollister-Stier Laboratories and Al-Center (brand name) made by Center Laboratories are both readily available. The Alpyral has a concentration of 20,000 PNU (protein nitrogen units) per ml., while the Al-Center antigen has a concentration of 10,000 PNU per ml. The former is often preferred, since the volume of suspension needed for a response is less. Therefore, the patient suffers less discomfort at the injection site.

The instructions of the manufacturer are followed in the usual manner to initiate treatment. The most common protocol requires administration of increasing dosage at intervals of 3-4 days (twice weekly). The doses are increased with each injection, usually beginning using increasing doses at 25 PNU, 75 PNU, 200 PNU, 500 PNU and 1,000 PNU. After dosage of 1000 PNU is reached, the antigen is administered at weekly intervals with progression to 2000 PNU, 4000 PNU and 6000 PNU. After dosage of 6000 PNU is reached, weekly injections at that dosage are given weekly until definite decrease in the amount of hair loss and improvement in condition of the scalp is observed.

Occasionally administration of 6000 PNU results in pain and swelling at the injection site. When this occurs, it is necessary to repeat a lower dosage several times before advancing to the 6000 PNU dosage. While discomfort caused by higher dosage is troublesome, serious side effects from use of house dust suspension has not been reported.

It should be noted that the sensitivity of patients to house dust antigen varies greatly. Some patients are very sensitive to house dust antigen, they may require far less antigen for treatment. In some instances the dosage required for maintenance was as little as 5 PNU until a favorable response was obtained. Determining the correct dosage may require use of very small amounts of antigen, possibly starting with 1 PNU dosage with continued decrease or increase in amount administered until the appropriate dosage is determined. Regardless of the dosage given initially for maintenance, as soon as results are clearly evidenced, it is wise to attempt to maintain progress with less frequent administration. If sufficient advantage is maintained with administration at two week intervals, it is desirable to administer the antigen even less frequently.

If no improvement in scalp condition or hair retention is noticed after about two months and if there is no undue discomfort at the injection site the maintenance dosage of the house dust antigen preparation may be increased to 8000 PNU. After two months at the 8000

PNU dosage level, the dosage can be increased to 10,000 PNU if results of treatment are not satisfactory.

If improvement in the scalp condition and hair retention is not seen in 12 months, it can be suspected that this treatment will not result in improvement. However, it should be noted that positive results have been initially noted at the end of two years of treatment.

Discussion

It is believed that failure to recognize and treat effects of house dust and testosterone allergies results in many cases of baldness and disfunction of the lubricating activity of the skin. The effects of house dust with its many air pollutants on skin and hair can now be treated in accord with the teachings of the invention. It is suggested that any patient presenting with unacceptable amount of hair loss and disturbance of the lubricating function of the skin should be considered as a candidate for desensitization treatment. If the patient is found, during skin testing, to be allergic to house dust, treatment in accord with the teachings using that allergen should be considered. However, if familial history of hair loss is reported, treatment with minidoses of testosterone should be considered.

The levels of testosterone used by the method of the invention do not in any way effect the hormonal balance of the body, since the amount of testosterone naturally produced and present in the body is so much higher than the minidoses delivered during treatment that the effect on systemic hormonal level is negligible.

Compositions containing the small amounts used in testing and treating patients can be provided in ampules, vials, or bottles with dropper tops for purposes of testing and treatment. The bottle with a top appropriate for dispensing the medication in drop form is particularly useful for dispensing the composition to the patient for self-administration. The vials or ampules with graduated concentration of the testosterone would be appropriate for dispensing to physicians for use in testing patients to determine dosage required.

I claim:

1. A method of treating hair loss or abnormal oil distribution on the skin or hair comprising the steps of:
   1) testing the patient for hypersensitivity to house dust and testosterone by administration of decreasing amounts of testosterone to the mucous membranes of the oral cavity and by administration of increasing doses of suspensions of house dust antigen;
   2) administering to a patient shown to have hypersensitivity in the antigen test performed in step 1 doses of antigen to which the patient shows hypersensitivity until the desensitizing dosage level is reached; and
   3) effecting treatment by the long-term administration of the desensitizing dose of antigen as determined in step 1.

2. A method of claim 1 wherein the antigen administered is testosterone and wherein the desensitizing dose is determined by administration of decreasing amounts of antigen.

3. A method of claim 1 wherein the testosterone preparation used in testing and treatment is an aqueous suspension of testosterone propionate.

4. Am method of claim 1 wherein the testosterone is administered by sublingual route.

5. A method of claim 1 wherein the maintenance dosage administered is between 0.0006 mg. and 1 mg every one to two days.

6. A method of claim 5 wherein the maintenance dose is between 0.008 mg. and 0.2 mg. every one or two days.

7. A pharmaceutical composition comprising 0.4 mg/ml to 0.012 mg/ml testosterone or an ester of testosterone in an aqueous pharmaceutically acceptable carrier in a sealed container.

8. A method of claim 1 wherein in addition to use of testosterone in desensitizing amounts a long term treatment is effected using 6000 to 10,000 PNU of house dust antigen in suspension.

9. A method of claim 1 wherein the long term treatment is effected using 6000 to 8000 PNU of house dust antigen in suspension.

10. A composition of claim 7 wherein the active agent is testosterone propionate.

11. A composition of claim 7 wherein the active agent is testosterone.

12. A composition of claim 7 wherein the container is a bottle having a top for dispensing the medication in drops.

13. A method of claim 1 wherein the long term treatment is effected using 5 PNU to 1000 PNU house dust antigen.

14. A method of claim 1 wherein the desensitizing dose is less than 0.0012 mg.

15. A method of claim 14 wherein the desensitizing dose is less than 0.006 mg.

16. A method of treating hair loss or abnormal oil distribution on the skin or hair comprising the steps of:
   1) administering to a patient suffering from male pattern androgenic baldness small doses of testosterone in aqueous solution to the mucosa to determine whether there is hypersensitivity to testosterone;
   2) administering to a patient who has shown hypersensitivity in step 1 decreasing amounts of testosterone or an ester thereof in aqueous solution to the mucosa until a desensitizing, non-provoking dose is reached; and
   3) treating the patient by administering to a patient desensitizing doses of testosterone in aqueous solution.

17. A kit of claim 1 wherein the compositions are provided in containers having a top for dispensing the medication in drops.

18. A method of claim 16 wherein the desensitizing dose is less than 0.0012 mg.

19. A method of claim 16 wherein the desensitizing dose is less than 0.0006 mg.

* * * * *